United States Patent [19]

Büchel et al.

[11] 4,183,940
[45] Jan. 15, 1980

[54] ANTIMYCOTIC IMIDAZOLYL-9,10-DIHYDRO-ANTHRACENE DERIVATIVES

[75] Inventors: Karl H. Büchel; Wolfgang Krämer; Manfred Plempel; Ingo Haller, all of Wuppertal, Fed. Rep. of Germany

[73] Assignee: Bayer Aktiengesellschaft, Leverkusen, Fed. Rep. of Germany

[21] Appl. No.: 840,461

[22] Filed: Oct. 7, 1977

[30] Foreign Application Priority Data

Oct. 30, 1976 [DE] Fed. Rep. of Germany ....... 2650171

[51] Int. Cl.$^2$ ................. A61K 31/415; C07D 233/56; C07D 233/60
[52] U.S. Cl. ................. 424/273 R; 548/336; 548/345; 548/262; 424/269
[58] Field of Search ............................. 548/345, 336; 424/273 R

[56] References Cited

U.S. PATENT DOCUMENTS

| | | | |
|---|---|---|---|
| 3,647,816 | 3/1972 | Draber et al. | 548/345 |
| 3,764,609 | 10/1973 | van der Stelt | 548/345 |
| 3,778,447 | 12/1973 | Draber et al. | 548/345 |
| 3,821,394 | 6/1974 | Timmler et al. | 424/273 |
| 4,049,418 | 9/1977 | Timmler et al. | 548/345 |

OTHER PUBLICATIONS

Draber et al., Chem. Abst. 1970, vol. 73, No. 45510q.

*Primary Examiner*—Alan L. Rotman
*Assistant Examiner*—Natalia Harkaway
*Attorney, Agent, or Firm*—Sprung, Felfe, Horn, Lynch & Kramer

[57] ABSTRACT

The invention provides new azolyl-9,10-dihydroanthracene derivatives of the formula

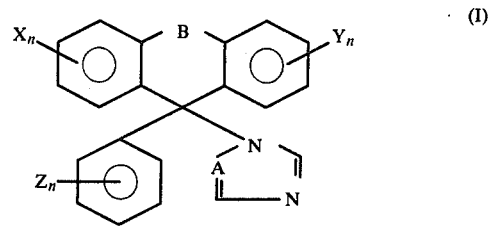

in which
A represents a CH group or a nitrogen atom,
B represents a CO group or a group of the formula:

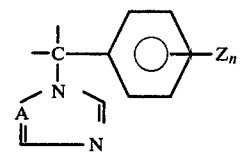

X, Y and Z are identical or different and represent halogen, alkyl, halogenoalkyl, alkoxy, or alkylthio and n represents 0 or an integer of from 1 to 4, and their salts.

Also included in the invention are methods for the preparation of said compounds, compositions containing said compounds and methods for their use. The compounds of the invention have antimycotic activity.

11 Claims, No Drawings

ANTIMYCOTIC IMIDAZOLYL-9,10-DIHYDRO-ANTHRACENE DERIVATIVES

The present invention relates to new azolyl-9,10-dihydro-anthracene derivatives and their salts, a process for their preparation and their use as medicaments, in particular as antimycotics.

It has already been disclosed that certain imidazolyl-dibenzo derivatives, such as, for example, 10-imidazol-1-yl-10-phenyl-xanthine and -thioxanthine or 9-imidazol-1-yl-9-(4-methyl-thiophenyl)-fluorene and 5-imidazol-1-yl-5-(4-methylthiophenyl)-[a,d]-dibenzocycloheptane, have a good antimycotic action (compare German Offenlegungsschrift (German Published Specification) No. 1,811,654). However, their action, in particular against dermatophytes and in vivo against Candida, is not always completely satisfactory.

According to the present invention, we provide azolyl-9,10-dihydro-anthracene derivatives of the formula

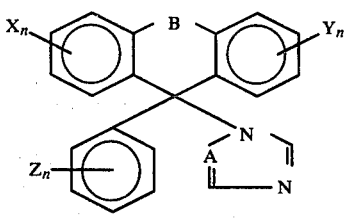

in which
A represents a CH group or a nitrogen atom,
B represents a CO group or a group of the formula:

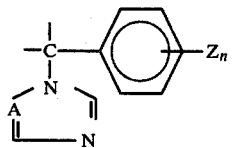

X, Y and Z are identical or different and represent halogen, alkyl, halogenoalkyl, alkoxy, or alkythio and n represents 0 or an integer of from 1 to 4, and their salts.

The compounds of the invention (i.e. the compounds of the formula (I) and their salts) have strong antimycotic properties. Consequently, of those compounds which are salts the pharmaceutically tolerable salts are most important, and preferred.

Furthermore, it has been found that the new azolyl-9,10-dihydro-anthracene derivatives can be synthesized if anthracen-derivatives of the formula

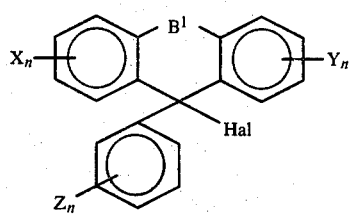

in which
X, Y, Z and n have the meaning indicated above, $B^1$ represents the CO group or the grouping

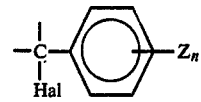

and Hal represents chlorine or bromine,
are reacted with azoles of the formula

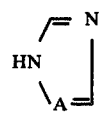

in which
A has the meaning indicated above,
optionally in the presence of an acid-binding agent and optionally in the presence of a diluent.

Compounds in which the radical B represents the grouping

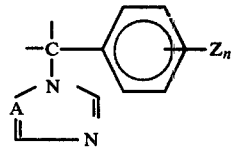

can be present in the cis (meso)-form or trans-form or as mixtures of the two forms.

Surprisingly, the azolyl-9,10-dihydro-anthracene derivatives according to the invention exhibit a better antimycotic, therapeutically useful activity than imidazolyldibenzo derivatives which are known from the state of the art, such as, for example, 10-imidazol-1-yl-10-phenyl xanthine and -thioxanthine or 9-imidazol-1-yl-9-(4-methylthiophenyl)fluorene and 5-imidazol-1-yl-5-(4-methylthiphenyl)-[a,d]-dibenzocycloheptane, which are closely related compounds chemically and from the point of view of their action.

If 9-chloro-9-(4-chlorophenyl)-9,10-dihydro-10-oxoanthracene and imidazole are used as the starting materials, the course of the reaction can be represented by the following equation:

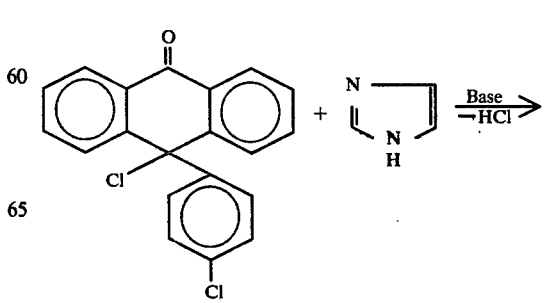

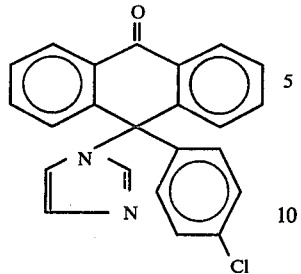

If 9,10-dichloro-9,10-dihydro-9,10-diphenyl-anthracene and imidazole are used as the starting materials, the course of the reaction can be represented by the following equation:

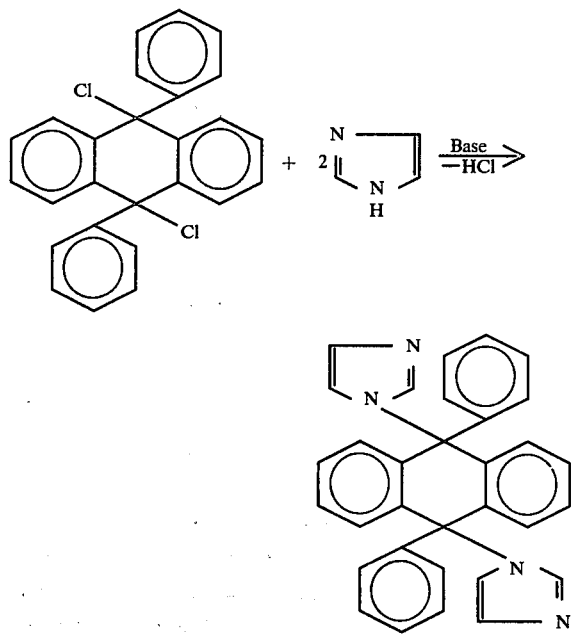

The formula (II) provides a general definition of the 9,10-dihydro-anthracene derivatives to be used as starting materials. In this formula, X, Y and Z are identical or different and preferably represent halogen, especially fluorine, chlorine and bromine; alkyl with 1 to 4 carbon atoms, methyl, ethyl, isopropyl and tert.-butyl being mentioned as examples; halogenoalkyl with up to 4 carbon atoms and up to 5 halogen atoms, in particular with 1 or 2 carbon atoms and up to 3 identical or different halogen atoms, halogen atoms being, in particular, fluorine and chlorine, an example which may be mentioned being trifluoromethyl; and, preferably, alkoxy and alkythio with 1 to 4, in particular 1 to 2, carbon atoms. The index n preferably represents 0, 1, 2 or 3. $B^1$ and Hal are as defined previously.

The 9,10-dihydro-anthracene derivatives which can be used according to the invention as starting materials are known (compare Beilstein H7, 530, E II 493; H5, 754, E II 681 and the literature sources quoted there) or they can be prepared by the customary methods indicated there. They are obtained, for example, by chlorinating or brominating 9,10-dihydro-anthracene derivatives of the formula

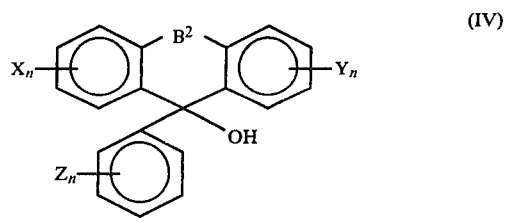

in which
X, Y, Z and n have the meaning indicated above and $B^2$ represents the CO group or the grouping

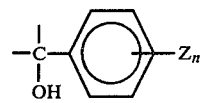

The 9,10-dihydro-anthracene derivatives of the formula (IV) are also known (compare Beilstein H6, 1061; H7, II 713; H8, 215 and the literature sources quoted there) or they can be prepared by the customary methods indicated there. They are obtained by reacting the particular anthraquinones with the corresponding Grignard compounds. The 9,10-dihydro-anthracene derivatives of the formula (IV), in which $B^2$ represents the CO group, are obtained when 1 mol of Grignard compound is employed per 1 to 2 mols of anthraquinone, and those in which $B^2$ represents the

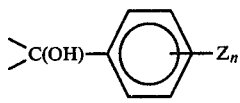

grouping are obtained when 2 mols of Grignard compound are employed per 1 mol of anthraquinone.

Examples which may be mentioned of the 9,10-dihydro-anthracene derivatives of the formula (II) to be used according to the invention as starting materials are: 9-chloro-9,10-dihydro-10-oxo-9-phenyl-anthracene, 9-bromo-9,10-dihydro-10-oxo-9-phenyl-anthracene, 9-chloro-9-(4-chlorophenyl)-9,10-dihydro-10-oxo-anthracene, 9-chloro-9-(3-chlorophenyl)-9,10-dihydro-10-oxo-anthracene, 9-chloro-9-(2-chlorophenyl)-9,10-dihydro-10-oxo-anthracene, 9-chloro-9,10-dihydro-9-(3-methylphenyl)-10-oxo-anthracene, 9-chloro-9,10-dihydro-9-(4-methylphenyl)-10-oxo-anthracene, 9-chloro-9-(2-4-dichlorophenyl)-9,10-dihydro-10-oxo-anthracene, 9-chloro-9-(2,3-dichlorophenyl)-9,10-dihydro-10-oxo-anthracene, 9-bromo-9-(4-bromophenyl)-9,10-dihydro-10-oxo-anthracene, 9-chloro-9,10-dihydro-9-(4-fluorophenyl)-10-oxo-anthracene, 9-chloro-9,10-dihydro-10-oxo-9-(3-trifluoromethyl-phenyl)-anthracene, 9-chloro-9,10-dihydro-9-(4-methoxyphenyl)-10-oxo-anthracene, 9-chloro-9,10-dihydro-9-(4-methylthiophenyl)-10-oxo-anthracene, 9-chloro-9,10-dihydro-9-(2-isopropylphenyl)-10-oxo-anthracene, 9-chloro-9,10-dihydro-9-(3-isopropylphenyl)-10-oxo-anthracene, 9-chloro-9,10-dihydro-9-(4-isopropylphenyl)-10-oxo-anthracene, 9,10-dihydro-10-oxo-9-phenyl-1,5,9-trichloroanthracene, 9,10-dichloro-9,10-dihydro-9,10-diphenyl-anthracene, 9,10-dibromo-9,10-dihydro-9,10-diphenyl-anthracene, 9,10-dichloro-9,10-[di(4-chlorophenyl)]-9,10- dihydro-anthracene and 9,10-dichloro-9,10-[di(2-methylphenyl)]-9,10-dihydro-anthracene.

The formula (III) provides a general definition of the azoles which are also to be used as starting materials. In this formula, A has the meaning indicated in the definition of the invention.

The azoles of the formula (III) which can be used according to the invention are compounds which are generally known in organic chemistry.

The most important salts of the compounds of the formula (I) are the salts of physiologically acceptable acids. These include, preferably, the hydrogen halide acids, such as, for example, hydrochloric acid and hydrobromic acid, especially hydrochloric acid, phosphoric acid, nitric acid and monofuctional and bifunctional carboxylic acids and hydroxycarboxylic acids, such as, for example, acetic acid, maleic acid, succinic acid, fumaric acid, citric acid, salicyclic acid, pamoic acid, sorbic acid, tartaric acid and lactic acid, and 1,5-napthalenedisulphonic acid. These or other salts, for example the picrates, can also be used for purification of the bases obtained; the bases are converted into salts, the salts are separated and the bases are liberated from the salts.

The salts of the compounds of the formula (I) can be obtained in a simple manner according to customary salt formation methods, for example by dissolving the base in ether, for example diethyl ether, and adding the acid, for example nitric acid, and can be isolated in a known manner, for example by filtration, and can optionally be purified.

Diluents which can be used for the reaction according to the invention are inert organic solvents. These include, preferably, ketones, such as diethyl ketone, and in particular acetone and methyl ethyl ketone; nitriles, such as propionitrile, and in particular acetonitrile; alcohols, such as ethanol or isopropanol; ethers, such as tetrahydrofurane or dioxane; benzene; formamides, such as, in particular, dimethylformamide, and halogenated hydrocarbons.

The reaction according to process (a) is carried out in the presence of an acid-binding agent. It is possible to add all inorganic or organic acid-binding agents which can customarily be used, such as alkali metal carbonates, for example sodium carbonate and potassium carbonate, and sodium bicarbonate, or such as lower tertiary alkylamines, cycloalkylamines or aralkylamines, for example triethylamine, N,N-dimethyl-benzylamine or dicyclohexylamine; or such as pyridine and diazabicyclooctane. An appropriate excess of azole is preferably used.

The reaction temperatures in the process according to the invention can be varied within a relatively wide range. In general, the reaction is carried out from about 20° to 150° C., preferably at about 20° to 100° C.

In carrying out the process according to the invention, about 1 to 3 mols of azole and about 1 to 3 mols of acid-binding agent are preferably employed per 1 mol of the compound of the formula (II). In order to isolate the compounds of the formula (I) the solvent is distilled off, the residue is taken up in an organic solvent and the organic solvent is washed several times with water, dried and freed from solvent in vacuo. The residue is worked up by methods which are generally customary and is optionally purified by distillation or recrystallisation.

The compounds of the formula (I) according to the invention, and their salts, have antimicrobial, in particular strong antimycotic, effects. They posses a very broad antimycotic spectrum of activity, especially against dermatophytes and blastomyces, for example against varieties of Candida, such as *Candida albicans,* varieties of Epidermophyton, such as *Epidermophyton floccosum,* varieties of Aspergillus, such as *Aspergillus niger* and *Aspergillus fumigatus,* varieties of Trichophyton, such as *Trichophyton mentagrophytes,* varieties of Microsporon, such as *Microsporon felineum* and varieties of Penicillium, such as *Penicillium commune.* The recital of these micro-organisms in no way implies a limitation of the germs which can be combated but is only of illustrative character.

The compounds according to the invention can, therefore, be employed with good success against fungal infections in warm-blooded animals.

The following may be mentioned as examples of fields of indication in medicine: dermatomycoses and systemic mycoses, particularly those caused by *Trichophyton mentagrophytes* and other varieties of Trichophyton, varieties of Microsporon, *Epidermophyton floccosum,* blastomyces and biphase fungi as well as moulds.

The present invention provides a pharmaceutical composition containing as active ingredient a compound of the invention in admixture with a solid or liquified gaseous diluent, or in admixture with a liquid diluent other than a solvent of a molecular weight less than 200 (preferably less than 350) except in the presence of a surface-active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylforimamide, oils [for example, ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The daily dose for administration of the medicaments of the invention is 0.5 g to 30 g of active ingredient. Preferred doses are 3 times 20 to 3 times 40 mg/kg daily.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably parenterally, especially intravenously. Preferred pharmaceutical compositions and medicaments are therefore those adapted for parenteral administration.

In general it has proved advantageous, in medicine, to administer the active compound or compounds according to the invention in total amounts of about 1 to about 300, preferably 50 to 200, mg/kg of body weight every 24 hours, optionally in the form of several individual administrations, to achieve the desired results.

It can, however, be necessary to deviate from the dosages mentioned and in particular to do so as a function of the species and the body weight of the subject to be treated, the nature and severity of the disease, the nature of the formulation and the administration of the medicament, and the time or interval at which administration takes place. Thus it can in some cases suffice to manage with less than the abovementioned amount of active compound, whilst in other cases the abovementioned amount of active compound must be exceeded. Any expert can easily decide the particular requisite optimum dosage and method of administration of the active compounds on the basis of his expert knowledge.

EXAMPLE A

Antimycotic in vitro activity

Description of the experiment:

The invitro tests were carried out in a series dilution test with germ inocula of an average of $5 \times 10^4$ germs/ml of substrate. The nutrient medium was (a) for dermatophytes and moulds: Sabouraud's milieu d 'epreuve and (b) for yeasts: meat extract/glucose broth.

The incubation temperature was 28° C. and the duration of incubation was 24 to 96 hours.

Table A:

Antimycotic in vitro activity

MIC values in $\gamma$/ml of nutrient medium for

| Active compound | *Trichophyton mentagrophytes* | Candida albicans | Penicillium commune | Aspergillus species | *Microsporon felineum* |
|---|---|---|---|---|---|
| 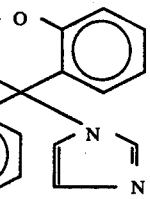 (known) | >100 | 20 | 100 | — | >100 |
| 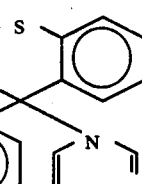 (known) | >100 | 40 | >100 | — | >100 |
| 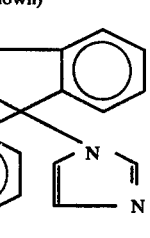 (known) | <4 | 100 | >100 | >100 | 20 |
| 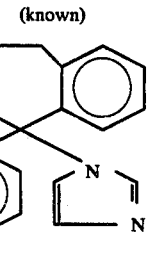 (known) | 10 | — | >100 | >100 | 40 |
| 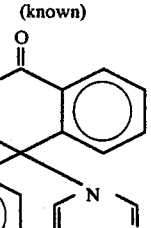 (3) | <1 | 4 | 4 | 4 | 8 |

Table A:-continued
Antimycotic in vitro activity
| | MIC values in γ/ml of nutrient medium for | | | | |
|---|---|---|---|---|---|
| Active compound | Trichophyton mentagrophytes | Candida albicans | Penicillium commune | Aspergillus species | Microsporon felineum |
| 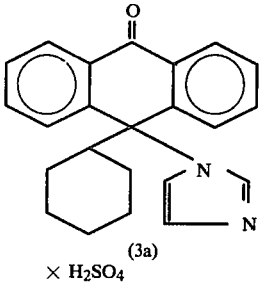 (3a) × H₂SO₄ | <1 | 8 | 8 | 32 | <1 |
|  (3b) × 2 H₃PO₄ | <1 | >64 | 8 | 64 | 4 |
| 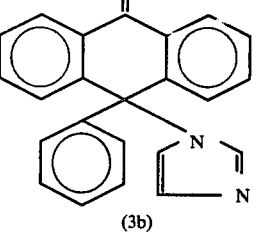 (3c) × HCl | <1 | >64 | 8 | 32 | 4 |
| 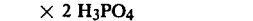 (4) | <1 | >64 | >64 | >64 | <1 |
| 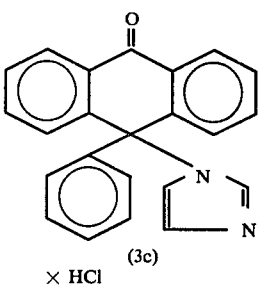 (4a) × 2 H₃PO₄ | <1 | 32 | 4 | >64 | 1 |

Table A:-continued

| | Antimycotic in vitro activity | | | | |
|---|---|---|---|---|---|
| | MIC values in γ/ml of nutrient medium for | | | | |
| Active compound | Trichophyton mentagrophytes | Candida albicans | Penicillium commune | Aspergillus species | Microsporon felineum |
| 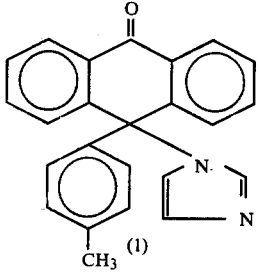 (1) | <1 | 64 | 64 | >64 | 8 |
| 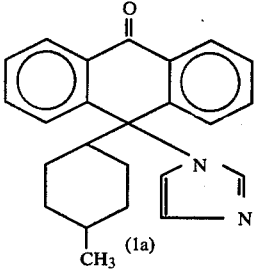 (1a) | <1 | >64 | 8 | >64 | 4 |
| 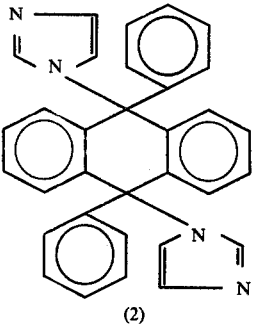 (2) × 2 H$_3$PO$_4$ | 32 | 4 | >64 | — | — |

EXAMPLE B

Antimycotic in vivo activity (oral) in candidosis of mice

Description of the experiment:

Mice of the type SPF-CF$_1$ were infected intravenously with $1-2\times 10^6$ logarithmically growing Candida cells, which were suspended in physiological sodium chloride solution. The animals were treated orally one hour before and seven hours after the infection with, in each case, 100 mg/kg of body weight of the formulations.

Untreated animals died from the infection 2 to 6 days after infection. The survival rate on the 6th day after infection was about 5% in the case of the untreated control animals.

Explanation of symbols

+++++ = very good action = ≧90% of survivors on the 6th day after infection

++++ = good action = ≧80% of survivors on the 6th day after infection

+++ = action = ≧60% of survivors on the 6th day after infection

++ = poor action = ≧40% of survivors on the 6th day after infection

+ = trace of action n.a. = no action

Table B:

| Antimycotic in vivo activity (oral) in candidosis of mice | |
|---|---|
| Active compound | Action |
| 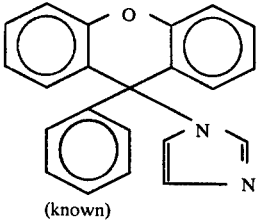 (known) | n.a. |

Table B:-continued

Antimycotic in vivo activity (oral) in candidosis of mice

| Active compound | Action |
|---|---|
| (known) [diphenyl sulfide imidazole structure] | n.a. |
| (known) [fluorene methylphenyl imidazole structure] | n.a. |
| (known) [dibenzosuberane methylphenyl imidazole structure] | n.a. |
| (3) [anthracenone phenyl imidazole structure] | +++ |
| (2) [bis-imidazolyl bis-phenyl anthracene structure] | ++ |
| (3 b) [anthracenone phenyl imidazole × 2 H₃PO₄] | +++ |
| (3 c) [anthracenone phenyl imidazole × HCl] | +++ |
| (4) [anthracenone (methylphenyl) imidazole, H₃C substituent] | + |

PREPARATION EXAMPLES

Example 1

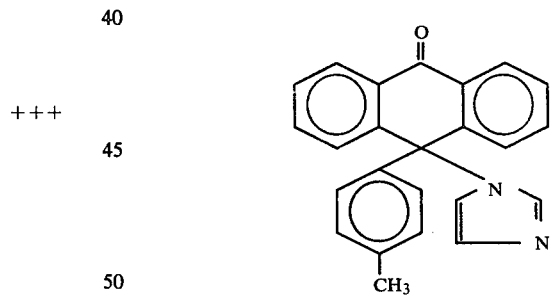

36.2 g (0.113 mol) of 9-chloro-9,10-dihydro-9-(4-methylphenyl)-10-oxo-anthracene and 20.4 g (0.3 mol) of imidazole in 400 ml of absolute acetonitrile are heated under reflux for 5 hours. Thereafter, the solvent is distilled off in vacuo and the residue is taken up in 500 ml of methylene chloride. The methylene chloride solution is washed twice with 1,000 ml of water each time and the organic phase is separated off, dried over sodium sulphate and concentrated by distilling off the solvent in vacuo. The yellow, oily residue is recrystallised from 300 ml of acetonitrile. 16.5 g (40.6% of theory) of 9,10-dihydro-9-imidazol-1-yl-9-(4-methylphenyl)-10-oxo-anthracene of melting point 200°–204° C. are obtained.

PREPARATION OF THE PRECURSOR

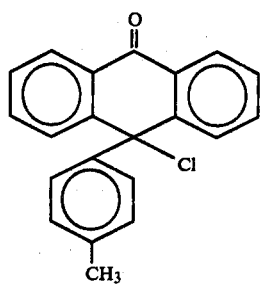

42 g (0.14 mol) of 9,10-dihydro-9-hydroxy-9-(4-methylphenyl)-10-oxo-anthracene and 20.2 g (107 mol) of thionyl chloride in 500 ml of methylene chloride are heated under reflux for 8 hours. Thereafter, the solvent is distilled off in vacuo and the solid which remains is recrystallised from petroleum ether. 36.2 g (70.9% of theory) of 9-chloro-9,10-dihydro-9-(4-methylphenyl)-10-oxo-anthracene of melting point 136°–140° C. are obtained.

PREPARATION OF THE STARTING MATERIAL

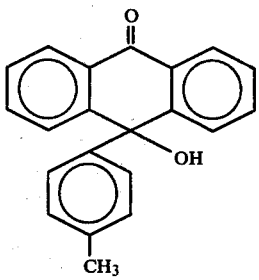

A Grignard solution, consisting of 85.5 g (0.5 mol) of 4-bromotoluene and 11.5 g of magnesium filings, is added dropwise to 104 g (0.5 mol) of anthraquinone in 2,000 ml of absolute toluene and 500 ml of absolute tetrahydrofurane at 80° C. After the dropwise addition has ended, the mixture is subsequently stirred for 6 hours at 80° C. The reaction mixture is then hydrolysed in 2,000 ml of ice water, containing hydrochloric acid. The organic phase is separated off, washed with water, dried over sodium sulphate and concentrated by distilling off the solvent in vacuo. The solid residue is recrystallised from acetonitrile. 32.5 g (21% of theory) of 9,10-dihydro-9-hydroxy-9-(4-methylphenyl)-10-oxoanthracene of melting point 203°–209° C. are obtained.

Example 1a

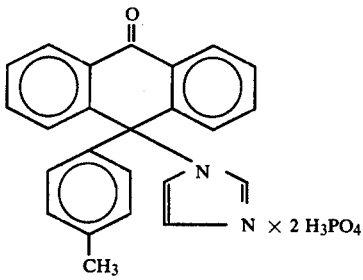

3.54 g of 85% strength phosphoric acid are added dropwise to 6 g (0.0172 mol) of 9,10-dihydro-9-imidazol-1-yl-9-(4-methylphenyl)-10-oxo-anthracene (compare Example 1) in 200 ml of methylene chloride and the mixture is subsequently stirred for 2 hours at room temperature. The solid which separates out is filtered off, washed with 150 ml of ether and 150 ml of acetone and dried over phosphorus pentoxide at 70° C. 7.8 g (83% of theory) of 9,10-dihydro-9-imidazol-1-yl-9-(4-methylphenyl)-10-oxo-anthracene diphosphate of melting point 171°–173° C. are obtained.

Example 2

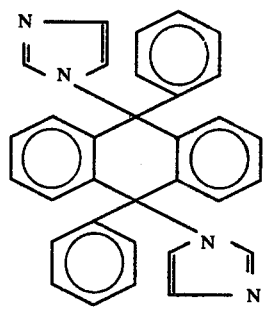

15 g (0.04 mol) of 9,10-dichloro-9,10-dihydro-9,10-diphenyl-anthracene and 17.7 g (0.24 mol) of imidazole in 250 ml of absolute acetonitrile are heated under reflux for 6 hours. Thereafter, the solvent is distilled off in vacuo and the residue is taken up in 500 ml of methylene chloride. The methylene chloride solution is washed twice with 500 ml of water each time and the organic phase is separated off, dried over sodium sulphate and concentrated by distilling off the solvent in vacuo. The residue is heated in 300 ml of methanol and filtered. The filtrate is concentrated and the oil which remains is triturated with 50 ml of diisopropyl ether, whereupon it crystallises. 10 g (54% of theory) of 9,10-diimidazol-1-yl-9,10-dihydro-9,10-diphenyl-anthracene of melting point 258°–260° C. are obtained.

The compounds of Table 1 which follows are correspondingly obtained.

Table 1

| Ex. No. | $X_n$ | $Y_n$ | $Z_n$ | A | B | Melting point (°C.) |
|---|---|---|---|---|---|---|
| 3 | — | — | — | CH | CO | 196–198 |
| 3a | — | — | — | CH | CO | 203–205 (× H₂SO₄) |
| 3b | — | — | — | CH | CO | 158–162 (× 2 H₃PO₄) |
| 3c | — | — | — | CH | CO | 203–205 (× HCl) |
| 4 | — | — | 2—CH₃ | CH | CO | 236 |
| 4a | — | — | 2—CH₃ | CH | CO | 218–221 (decomposition) (× 2 H₃PO₄) |
| 5 | — | — | — | N | CO | 190–191 |

Table 1-continued

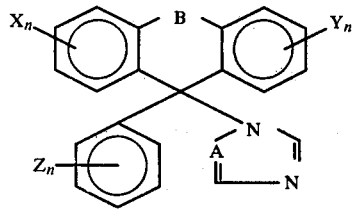

| Ex. No. | $X_n$ | $Y_n$ | $Z_n$ | A | B | Melting point (°C.) |
|---|---|---|---|---|---|---|
| 6 | — | — | — | N | —C(—phenyl)(imidazole) | 284–286 (trans) |
| 7 | — | — | — | N | —C(—phenyl)(imidazole) | 219–221 (cis, meso) |

Example 8

A typical pharmaceutical composition contains the following ingredients:
Compound according to example 3—1.0 gram
Isopropanol—59.0 gram
Water—35.0 gram
Glycerol—5.0 gram

What we claim is:

1. An azolyl-9,10-dihydroanthracene derivative of the formula I (I)

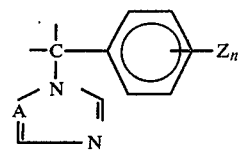

in which
A represents a CH group,
B represents a CO group or a group of the formula:

$$-\underset{\underset{N}{\overset{N}{\underset{\|}{\underset{A}{|}}}}}{C}-\text{phenyl}-Z_n$$

X, Y and Z are identical or different and each represents halogen, alkyl with 1 to 4 carbon atoms, halogenoalkyl with up to 4 carbon atoms and up to 5 halogen atoms, alkoxy with 1 to 4 carbon atoms or alkylthio with 1 to 4 carbon atoms and n represents 0 or an integer of from 1 to 4, or a pharmaceutically acceptable salt thereof.

2. A compound of claim 1 wherein X, Y and Z are identical or different and each represents halogen, alkyl with 1 to 4 carbon atoms, halogenoalkyl with up to 4 carbon atoms and up to 5 halogen atoms, alkoxy with 1 to 4 carbon atoms or alkylthio with 1 to 4 carbon atoms and n represents 0 or an integer from 1 to 3.

3. 9,10-Dihydro-9-imidazol-1-yl-9-phenyl-10-oxoanthracene or a pharmaceutically acceptable salt thereof.

4. A pharmaceutical composition for combatting mycoses comprising as an active ingredient, an effective amount of a compound of claim 1 in admixture with a solid or liquified gaseous diluent.

5. A pharmaceutical composition of claim 4, in the form of a sterile or isotonic aqueous solution.

6. A composition of claim 4 containing from 0.5 to 95% by weight of the said active ingredient.

7. A medicament for combatting mycoses in dosage unit form comprising an effective amount of a compound of claim 1 and an inert pharmaceutical carrier.

8. A medicament of claim 7 in the form of tablets, pills, dragees, capsules, ampoules, or suppositories.

9. A method of combating mycoses in warm-blooded animals in need of such treatment, which comprises administering to the animals an effective amount of a compound of claim 1 either alone or in admixture with a diluent or in the form of a medicament.

10. A method according to claim 9 in which the active compound is administered in an amount of from 10 to 300 mg per kg body weight per day.

11. A method according to claim 9 in which the active compound is administered parenterally.

* * * * *